United States Patent [19]

Mitchell et al.

[11] 4,046,872

[45] Sept. 6, 1977

[54] DENTAL CREAM

[75] Inventors: Robert Lee Mitchell, Somerset; William John Chung, Spotswood, both of N.J.

[73] Assignee: Colgate Palmolive Company, New York, N.Y.

[21] Appl. No.: 618,856

[22] Filed: Oct. 2, 1975

Related U.S. Application Data

[63] Continuation-in-part of Ser. No. 464,896, April 29, 1974, abandoned, which is a continuation-in-part of Ser. No. 369,705, June 13, 1973, abandoned.

[51] Int. Cl.$^2$ .............................................. A61K 7/18
[52] U.S. Cl. ................................. 424/52; 206/277; 424/57
[58] Field of Search .......................... 424/49–58; 206/277

[56] References Cited

U.S. PATENT DOCUMENTS

| 2,191,199 | 2/1940 | Hall | 424/57 |
|---|---|---|---|
| 2,941,926 | 6/1960 | Salzmann et al. | 424/57 |
| 3,227,617 | 1/1966 | Manahan et al. | 424/52 |
| 3,227,618 | 1/1966 | Manahan et al. | 424/52 |
| 3,624,199 | 11/1971 | Norfleet | 424/57 |
| 3,634,585 | 1/1972 | Manahan et al. | 424/52 |
| 3,662,060 | 5/1972 | Clippendale et al. | 424/57 |
| 3,678,155 | 7/1972 | Clippendale et al. | 424/52 |
| 3,822,345 | 7/1974 | Murray et al. | 424/52 |
| 3,864,471 | 2/1975 | King et al. | 424/52 |
| 3,941,877 | 3/1976 | King et al. | 424/52 |

FOREIGN PATENT DOCUMENTS

| 1,066,412 | 6/1954 | France | 424/57 |
|---|---|---|---|
| 777,556 | 6/1957 | United Kingdom | 424/52 |
| 1,132,830 | 11/1968 | United Kingdom | 424/52 |

OTHER PUBLICATIONS

Van Wazer "Phosphorus and its Compounds" (1961) vol. II, pp. 1644-1648, 1652-1653, vol. I, pp. 638-659, 665-678, 775-777, Interscience Publishers, Inc. N.Y., N.Y.

*Primary Examiner*—Shep K. Rose
*Attorney, Agent, or Firm*—Robert L. Stone; Murray M. Grill; Herbert S. Sylvester

[57] ABSTRACT

Dental cream comprising between about 35 and 60% by weight of abrasive consisting essentially of calcium carbonate and alumina, with the alumina at least about 0.05% by weight of the dental cream and in an amount not greater than the calcium carbonate. The dental cream also contains a water-soluble monofluorophosphate salt in an amount which provides about 0.01-1% by weight fluoride in said dental cream and about 0.1-1.5% by weight of an alkali metal tripolyphosphate as an agent to improve the ability of the dental cream to retain monofluorophosphate as fluoride. The dental cream may also contain 0.025-0.25% by weight of a dissolved or dispersed silicate.

22 Claims, No Drawings

DENTAL CREAM

This application is a continuation-in-part of Ser. No. 464,896, filed Apr. 29, 1974, now abandoned, which is a continuation-in-part of Ser. No. 369,705, filed June 13, 1973, now abandoned.

This invention relates to a dental cream containing a water-soluble monofluorophosphate.

Water-soluble monofluorophosphate salts, such as sodium monofluorophosphate, are desirable for use in dental creams in view of their ability to provide soluble monofluorophosphate as fluoride and to diminish the tendency of enamel to dissolve. However, many substances tend to react with water-soluble monofluorophosphate salts and to diminish its ability to provide soluble monofluorophosphate as fluoride. In choosing ingredients to be employed in monofluorophosphate dental creams, compatibility of such ingredients with the monofluorophosphate should be considered. Abrasive polishing materials have been proposed for monofluorophosphate toothpastes which contain calcium carbonate and alumina and particularly calcium carbonate at least in excess of the amount of alumina in view of the ability of monofluorophosphate dental creams containing such an abrasive or polishing system to retain soluble monofluorophosphate as fluoride.

It is an advantage of this invention that the ability of a monofluorophosphate dental cream to retain soluble monofluoridephosphate as fluoride is highly improved.

In prior practice, grades of calcium carbonate, particularly those which contain magnesium carbonate impurity caused compatibility problems with unlined aluminum containers when dental creams containing substantial amounts of such grades of calcium carbonate were placed therein. An advantage of a further aspect of this invention is that a dental cream is provided which is suitable for storage in an unlined aluminum container.

The present invention provides a dental cream composition comprising a dental cream vehicle having dispersed or dissolved therein a water-soluble monofluorophosphate salt in an amount which provides between about 0.01 and 1% of fluoride in said composition; between about 35 and 60% abrasive, said abrasive consisting essentially of calcium carbonate and alumina, said alumina being present in an amount not greater than said calcium carbonate and said alumina being in an amount of at least about 0.05%; and between about 0.1 and 1.5% of an alkali metal tripolyphosphate.

The inclusion in the dental cream composition of alumina in an amount of at least about 0.05%, and preferably at least about 1%, acts to stabilize the composition with consequent retention of active fluoride. Dental creams containing larger amounts of alumina retain the specified advantages. Stable dental creams having excellent characteristics are obtained with between about 7 and 13% alumina. Higher alumina content tends to improve the taste appeal characteristics of the dental cream, e.g., compositions containing from about 20% alumina up to the amount of the calcium carbonate.

Although the total amount of abrasive in the dental cream composition may be within the broad range of about 35–60%, it is preferred that it be within the range of about 40–52%. When larger amounts of abrasive are included in the composition, e.g., above about 54%, the composition tends to become unduly thick. Similarly, compositions containing less than about 40% abrasive tend to be too thin. The compositions containing the abrasive within the preferred range also preferably contain the preferred concentration of a gum. Increased amounts of gum tend to thicken the composition, and decreased amounts tend to make it less thick. When amounts of abrasive are used outside of the aforesaid preferred range, the consistency of the composition may be adjusted by a compensating change in the amount of gum.

The dental cream also contains an alkali metal (e.g. sodium or potassium) tripolyphosphate, preferably sodium tripolyphosphate ($Na_5P_3O_{10}$) in an amount between about 0.1 and 1.5% and preferably between about 0.15 and 1%. The tripolyphosphate stabilizes the dental cream to increase retention of soluble monofluorophosphate as fluoride. It is particularly preferred that the tripolyphosphate be in an amount of between about 0.2 and 0.7% to attain the desired dental cream stability. Larger amounts than about 1.5% tend to unduly thicken the dental creams.

Calcium carbonate in the form of chalk may be used. Chalk in the form of a powder having a particle size of between 1 and 10 microns is preferred. It is also preferred to use a grade of calcium carbonate of relatively high apparent specific gravity, e.g., about 0.9 to 1.2. If desired, calcium carbonate grades of lower apparent specific gravity, e.g., 0.7 to 0.9 may be used. "Apparent specific gravity" refers to the untamped specific gravity of the calcium carbonate. Calcium carbonate, particularly in the form of chalk, often contains magnesium carbonate as an impurity. Calcium carbonate containing even small quantities of magnesium carbonate, e.g., about 0.1–0.3%, tends to adversely affect the stability of the dental cream with consequent loss of active fluoride. The stable dental creams of the present invention tolerate small amounts of impurity, e.g., magnesium carbonate in amounts less than about 1%. However, it is preferred that the magnesium carbonate should be about 0.1–0.5% based on the calcium carbonate.

Furthermore, the presence of magnesium carbonate impurity in calcium carbonate or chalk tends to adversely affect the compatability of the dental cream with unlined aluminum surfaces in which it may be packaged. When magnesium carbonate impurity is present in amount of at least about 0.1% of the total calcium carbonate, it is desirable to include between about 0.025 and 0.25% of a dissolved or dispersed silicate in the dental cream in order to render it suitable for compatible use in an unlined aluminum container.

The alumina employed in accordance with the instant invention is small in particle size, i.e., at least about 85% of the particles are smaller than 20 microns and is preferably hydrated, such as that classified as Gibbsite (alpha alumina trihydrate) and normally represented chemically as $Al_2O_3 \cdot 3HO_2O$ or $Al(OH)_3$. The average particle size of Gibbsite is generally about 6 to 9 microns with the following particle size distribution:

<30 microns; 94–99% <20 microns; 85–93% <10 microns; 56–67% <5 microns; 28–40%

Other types of alumina which may be employed in accordance with the instant invention include kappa type alumina, gamma phase alumina, beta phase alumina and mixtures thereof with alpha alumina trihydrate. Microcyrstalline alumina having a mean particle size of as little as 0.3 micron or less with 90–95% of the particles being smaller than 0.5 micron may also be used. The alpha alumina trihydrate sold by Alcoa as C333 is a fine grade of Gibbsite and is particularly highly desirable. The average particle size of C333 alumina is about 2.5–8.5 microns. It is obtained by grinding of the grade of alumina trihydrate sold by Alcoa as C33.

Dental creams, and particularly those containing the preferred alumina, may contain a small amount, e.g., up to about 2% and preferably 0.7–1%, of a harder abrasive to enhance the polishing function of the dental cream. Useful polishing abrasives include calcined aluminum oxide and zirconium silicate.

The water-soluble monofluorophosphate salt is included in the composition in an amount to provide between 0.01 and 1% (preferably about 0.04–0.1%)fluoride. It is preferably an alkali metal monofluorophosphate such as sodium monofluorophosphate, lithium monofluorophosphate, potassium monofluorophosphate and ammonium monofluorophosphate. The preferred salt is sodium monofluorophosphate, $Na_2PO_3F$, which, as commercially available, may vary considerably in purity. It may be used in any suitable purity provided that any impurities do not substantially adversely affect the desired properties. In general, the purity is desirably at least about 80 %. For best results, it should be at least 85%, and preferably at least 90% by weight of sodium monofluorophosphate with the balance being primarily impurities or by-products of manufacture such as sodium fluoride, water-soluble phosphate salt, and the like. Expressed in another way, the sodium monofluorophosphate employed should have a total fluoride content of above 12%, preferably above 12.7%; a content of not more than 1.5%, preferably not more than 1.2% of free sodium fluoride; and a sodium monofluorophosphate content of at least 12%, preferably at least 12.1% all calculated as fluorine.

Other monofluorophosphate salts which have sufficient water solubility for use in the instant invention include calcium monofluorophosphate, magnesium monofluorophosphate and aluminum monofluorophosphate. In accordance with this invention, the term "monofluorophosphate" also includes monofluoropolyphosphates such as $Na_4P_3O_9F$, $K_4P_3O_9F$, $(NH_4)_4P_3O_9F$, $Na_3KP_3O_9F$, $(NH_4)_3NaP_3O_9F$ and $Li_4P_3O_9F$.

Typically, the monofluorophosphate is present in amount which provides about 0.01–1% fluorine to the dentifrice. Thus, sodium monofluorophosphate is present, typically, in amount of about 0.076 to about 7.6%.

Particularly when magnesium carbonate impurity is present in the calcium carbonate, the dental cream compositions will usefully contain an alkali metal silicate, preferably sodium silicate, in order to provide desirable compatibility with unlined aluminum containers. A typical sodium silicate is a hydrated sodium silicate in flake form containing $Na_2O.SiO_2.H_2O$ in a ratio of about 1:2–3.2:5. The silicate may also be obtained in an aqueous solution, e.g., 40% solids, and also may be formed in situ in the dental cream by adding precursors thereof. Silica in the form of very fine particles, e.g., fumed silica, which forms dispersions, e.g., of collodial size, may be used instead of the preferred silicate.

The dental cream compositions may contain the silicate, when calculated as sodium silicate in an amount between 0.025 and 0.25% (preferably 0.05–0.15%) with 0.5 to about 0.1% being especially preferred with compositions containing relatively low alumina, e.g., about 1%. Compositions containing relatively high alumina, e.g., 20% preferably contain about 0.15–0.2% silicate.

Suitable surface or detersive material may be included in the dentifrice compositions. Such compatible materials are desirable to provide additional detersive, foaming and antibacterial properties depending upon the specific type of surface active material and are selected similarly. These detergents are water-soluble organic compounds usually and may be anionic, nonionic or cationic in structure. It is preferred to use the water-soluble non-soap or synthetic organic detergents usually. Suitable detersive materials are known and include, for example, the water-soluble salts or higher fatty acid monoglyceride monosulfate detergent (e.g., sodium coconut fatty acid monoglyceride monosulfate), higher alkyl sulfate (e.g., sodium lauryl sulfate), alkyl aryl sulfonate (e.g., sodium dodecyl benzene sulfonate), higher fatty acid esters of 1,2-dihydroxy propane sulfonate (e.g., sodium coconut fatty acid ester of 1,2-dihydroxy propane sulfonate) and the like.

The various surface active materials may be used in any suitable amount, generally from about 0.05 to about 10% by weight, and preferably from about 0.5 to 5% by weight of the dentifrice composition, with about 1.5 to 2% especially preferred.

The dental cream composition may also contain at least one of the substantially saturated higher aliphatic acyl amides of lower aliphatic amino carboxylic acid compounds, such as those having 12 to 16 carbons in the acyl radical. The amino acid portion is derived generally from the lower aliphatic saturated monoamino-carboxylic acids having about 2 to 6 carbons, usually the monocarboxylic acid compounds. Suitable compounds are the fatty acid amides of glycine, sarcosine, alanine, 3-amino-propanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of the said amide material.

The liquids and solids forming the dental cream composition should be proportioned to form an extrudable creamy mass of desirable consistency. In general, liquids in the dental cream will comprise chiefly water, glycerine, sorbitol, propylene glycol, or the like, including suitable mixtures thereof. It is advantageous usually to use a mixture of both water and a binder or humectant such as glycerine and/or sorbitol. It is preferred to use glycerine or mixtures of a major portion of glycerine with a minor portion or sorbitol. The humectant is generally used in an amount between 20 and 25%, and preferably about 22%. The total liquid content will generally be about 20–65% by weight of the formulation, with water being in an amount to bring the total of components to 100%.

It is preferred to use also a gelling agent in dental creams such as the natural and synthetic gum and gum-like material, e.g., Irish moss, gum tragacanth, sodium carboxymethylcellulose, polyvinylpyrrolidone, starch and the like; all being referred to as "gum." The Irish moss and sodium carboxymethylcellulose are compatible particularly and are preferred gelling agents. The gum content is usually in an amount up to about 10% and preferably about 0.5–5% by weight of the formulation, with gum in an amount of about 0.9–1.3% especially preferred.

The total of liquid and gelling agent (gum) form the dental cream vehicle in which the other components are dispersed or dissolved.

Various other materials may be incorporated in the dental creams of this invention. Examples thereof are coloring or whitening agents, preservatives, silicones, chlorophyll compounds and ammoniated materials such as urea, diammoniumphosphate and mixtures thereof. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01 to about 5%, preferably about 0.05 to about 1.0%, by weight of the dentifrice composition include:

$N^1$-4(chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
$N^1$-p-chlorphenyl-$N^5$-laurylbiguanide;
5-amino-1,3-bis (2-ethylhexyl)-5-methylhexahydropyrimidine;
and their nontoxic acid addition salts.

Any suitable flavoring or sweetening materials may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agent may together comprise from about 0.01 to 5% or more of the instant invention.

The dental cream should have a pH practical for use. The range is preferably alkaline and may range up to about 10. The dental creams containing the preferred amount of the tripolyphosphate typically have a range between about 9.6 to 9.9. The reference to the pH is meant to be the pH determination directly on the dental cream.

The instant dental cream compositions are highly efficacious in use. They exhibit desirable anti-caries, cosmetic and rheologic properties and may be stored and dispensed from conventional style collapsible unlined aluminum tubes.

The dental cream compositions may be prepared by conventional manufacturing methods, as disclosed in Chapter XV of Sagarin's Cosmetics, Science and Technology (1957), Interscience Publishers, Inc.

The following specific examples are further illustrative of the nature of the present invention, but it is to be understood that the invention is not limited thereto. All percentages and amounts of the various ingredients in the specification are by weight based on the total dental cream composition unless otherwise specified. The dental cream compositions of this invention are prepared in the conventional manner, namely by admixing solid and liquid components with the gum and mixing until swelling occurs with the formation of a gel, and then adding the abrasives and forming a homogeneous mixture.

In the process of preparing the dental cream compositions, it is noteworthy that alkali metal tripolyphosphate is dissolved in the dental vehicle in amount between about 0.1 and 1.5% in order to increase the ability of the dental cream to retain soluble monofluorophosphate as fluoride.

Example 1

| | % |
|---|---|
| calcium carbonate (chalk) | 42.5 |
| hydrated alumina | 1 |
| sodium tripolyphosphate | 0.2 |
| sodium silicate | 0.2 |
| glycerine | 22 |
| sodium benzoate | 0.5 |
| sodium saccharin | 0.2 |
| sodium carboxymethyl cellulose | 1.1 |
| sodium monofluorophosphate | 0.76 |
| detergent | 2 |
| flavor | 0.9 |
| water (to make up 100%) | |

The monofluorophosphate provides 0.1% of fluoride in the dental cream. The dental cream was packaged in an unlined aluminum tube and aged at an elevated temperature in an accelerated aging test. The composition is stable, retaining a high level of active fluoride and did not attack the inner unlined surface of the aluminum tubes.

EXAMPLES 2–7

Dental creams are prepared following the standardized development formulation, with the following percentages of the hydrated alumina and of the calcium carbonate (chalk);

| | Examples | | | | | |
|---|---|---|---|---|---|---|
| | 2 | 3 | 4 | 5 | 6 | 7 |
| alumina | 0.5% | 5% | 8% | 10% | 13% | 26% |
| chalk | 52% | 38% | 34% | 32.5% | 39% | 26% |

The dental creams of Examples 4 and 5 evidenced an unusually high level of fluoride stability.

The effective ranges of sodium silicate and of sodium tripolyphosphate were determined by testing over the specified ranges.

Other tests determined that the specified alternate components, e.g., fumed silica in place of sodium silicate and glycerine-sorbitol mixtures in place of glycerine provide stable dental cream compositions.

EXAMPLE 8

The following stable dental cream is prepared by standardized development formulation technique:

| | Parts |
|---|---|
| Glycerine | 22.00 |
| Sodium benzoate | 0.50 |
| Sodium saccharin | 0.20 |
| Sodium carboxymethyl cellulose | 1.50 |

-continued

| | Parts |
|---|---|
| Sodium monofluorophosphate | 0.76 |
| Sodium tripolyphosphate | 0.20 |
| Sodium silicate | 0.20 |
| Calcium carbonate | 17.50 |
| Hydrated alumina | 17.50 |
| Sodium lauryl sulfate | 1.50 |
| Flavor | 1.00 |
| Water | 0.5 to 100 |

It will be apparent to one skilled in the art that various modifications of the foregoing examples may be made thereto.

We claim:

1. A process of preparing a dental cream composition containing a monofluorophosphate salt which dental cream retains soluble monofluorophosphate as fluoride which dental cream comprises a dental cream vehicle, a water soluble monofluorophosphate salt, abrasives and alkali metal tripolyphosphate comprising dissolving in said dental cream vehicle containing said monofluorophosphate salt and said abrasives an alkali metal tripolyphosphate whereby there is dispersed or dissolved in said vehicle said alkali metal tripolyphosphate salt as a component which increases retention of soluble monofluorophosphate as fluoride, said monofluorophosphate salt being selected from the group consisting of alkali metal, calcium, magnesium and aluminum monofluorophosphate and present in an amount which provides between about 0.01 and 1% by weight of fluoride in said composition, said abrasives being in amount between about 35 and 60% by weight, said abrasive consisting essentially of calcium carbonate and alumina, said alumina being present in an amount of at least about 0.05% by weight up to an amount equal to or less than but not greater than said calcium carbonate, and said alkali metal tripolyphosphate being in amount between about 0.1 and 1.5% by weight.

2. The process of claim 1 containing at least about 1% by weight of alumina.

3. The process of claim 1 containing between about 40 and 52% by weight of abrasive; and wherein said alumina is hydrated alumina.

4. The process of claim 3 contains at least about 1% by weight of alumina.

5. The process of claim 4 containing between about 0.15 and 1% by weight of sodium tripolyphosphate.

6. The process of claim 5 containing between about 7 and 13% by weight alumina.

7. The process of claim 5 containing up to 20% by weight alumina.

8. The process of claim 5 containing more than 20% by weight alumina.

9. The process of claim 1 wherein said vehicle contains between about 20 and 25% by weight of a humectant; between about 0.5 and 5% by weight of a gum; and water.

10. The process of claim 9 wherein said alumina is hydrated alumina; and containing between about 0.15 and 1% by weight of said tripolyphosphate and between about 0.9 and 1.3% by weight of said gum.

11. The process of claim 10 containing between about 40 and 52% of said abrasive; wherein said tripolyphosphate is sodium tripolyphosphate; wherein said water-soluble monofluorophosphate is sodium monofluorophosphate; wherein said calcium carbonate is chalk which contains up to about 0.5% of its weight of magnesium carbonate; and wherein said dental cream contains between about 0.025 and 0.25% by weight of a dissolved or dispersed sillicate.

12. The process of claim 11 wherein said silicate is sodium silicate.

13. The process of claim 12 containing up to 20% by weight of said alumina, between about 0.2 and 0.7% by weight of sodium tripolyphosphate and between about 0.05 and 0.15% by weight of sodium silicate.

14. The process of claim 12 containing between about 7 and 13% by weight of said alumina and between about 0.05 and 0.1% by weight of said sodium silicate.

15. The process of claim 11 wherein said humectant contains glycerine and said chalk contains at least about 0.1% of its weight of magnesium carbonate.

16. The process of claim 12 containing about 1% by weight of said alumina and between about 0.05 and 0.1% by weight of said sodium silicate.

17. The process of claim 16 wherein said humectant contains glycerine and said chalk contains at least about 0.1% of its weight of magnesium carbonate.

18. The process of claim 12 containing more than 20% by weight of said alumina, between about 0.2 and 0.7% by weight of said sodium tripolyphosphate, and between about 0.15 and 0.2% by weight of said sodium silicate.

19. The process of claim 18 wherein said humectant contains glycerine and said chalk contains at least about 0.1% of its weight of magnesium carbonate.

20. A process of preparing a dental cream composition containing a monofluorophosphate salt which dental cream retains soluble monofluorophosphate as fluoride which dental cream comprises a dental cream vehicle, a water soluble monofluorophosphate salt, abrasives and sodium tripolyphosphate comprising dissolving in said dental cream vehicle containing said monofluorophosphate salt and said abrasives sodium tripolyphosphate whereby there is dispersed or dissolved in said vehicle said sodium tripolyphosphate as a component which increases retention of soluble monofluorophosphate as fluoride, said monofluorophosphate salt being selected from the group consisting of alkali metal, calcium magnesium and aluminum monofluorophosphate and present in an amount which provides between about 0.01 and 1% by weight of fluoride in said composition said abrasives being in amount between about 35 and 60% by weight, said abrasive consisting essentially of at least about 26% by weight of the dental cream composition of calcium carbonate and between about 0.05 and 26% by weight of alumina and said sodium tripolyphosphate being in amount between about 0.1 and 1.5% by weight.

21. The process of claim 1 wherein said alkali metal tripolyphosphate is sodium tripolyphosphate.

22. The process of preparing a dental cream composition as claimed in claim 1 wherein said dental cream is packaged in an unlined aluminum tube.

* * * * *